United States Patent [19]

Mikkelsen

[11] Patent Number: Plant 5,869

[45] Date of Patent: Jan. 27, 1987

[54] IMPATIENS PLANT NAMED TWILIGHT

[75] Inventor: James C. Mikkelsen, Ashtabula, Ohio

[73] Assignee: Mikkelsens, Inc., Ashtabula, Ohio

[21] Appl. No.: 663,708

[22] Filed: Oct. 19, 1984

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

An impatiens plant named Twilight, having red and light pink bicolor flowers, distinct variegated leaves, vigorous, highly self-branching dense bush growth habit making it useful for pot, hanging basket and bedding plant use; and by its adaptability to various environments of use.

2 Drawing Figures

The present invention relates to a new and distinctive cultivar of New Guinea Impatiens plant, botanically known as Impatiens, and referred to by the cultivar named Twilight.

Twilight was developed by me in Ashtabula, Ohio, through controlled breeding by crossing Mikkelsen Seedling No. 80-439-4 (seed parent)×Mikkelsen Seedling No. 80-428-2 (pollen parent). Asexual reproduction by terminal or stem cuttings taken by me in Ashtabula, Ohio, has shown that the unique features of this new impatiens are stabilized and are reproduced true to type in successive propagations.

The following characteristics distinguish the new impatiens from both its parent varieties and other cultivated impatiens of this type known and used in the floriculture industry:

1. Larger, more vigorous growing plant than Pulsar, Quasar, and Columbia, and more compact with better branching than Astro, Eclipse and Enterprise. Astro, Columbia and Eclipse are disclosed in U.S. Plant Pat. Nos. 5,126 and 4,689, respectively, and the other cultivars referred to are disclosed in pending applications.

2. Flower color is a distinct variegated or bicolor red and light pink, with the pink and the infused colors being deeper than the color in Astro. The flower size is larger than Eclipse and similar in size to Enterprise and Astro.

3. Flowers have good keeping quality and tend to nestle in the foliage as they mature, similar to the flowering of Astro.

4. The new cultivar is highly self-branching, and a vigorous grower with a bush growth habit. Plant is more dense than either Eclipse or Astro, and is ideal for small pots, baskets and bedding plant use.

5. Leaf color is a bronze purple with a golden bronze distinct variegation at the midrib which is darker than Astro, but not as dark as Eclipse and Enterprise.

6. The leaves are shorter and broader than any of the other dark leaved varieties like Eclipse, Astro and Enterprise. The leaf has a red midrib and veins similar to Astro.

7. Plants and flowers have good low temperature tolerance as demonstrated by the ability to continue flowering after two nights of 2.2° C. after planting out in early May.

8. Flowering begins earlier than Astro and Eclipse, but is not as early as Quasar, Pulsar or Solared, the latter being disclosed in U.S. Plant Pat. No. 5,131.

9. Twilight is an excellent cultivar to use for further hybridization in the development of bicolors because of the contrast between the colors on the flower and its growth habit, leaf variegation and leaf shape.

10. Upper leaf surface is pubescent, a characteristic which is not present in the cultivars referred to above for which applications have been filed. In these other cultivars, the upper surface is rugose.

In the accompanying color photographs,

Sheet 1 (taken July, 1983) illustrates in perspective view the overall appearance of Twilight.

Sheet 2 comprises a close-up view of two flowers of Twilight, very accurately depicting the true flower color indicated below by color values. The photograph comprising sheet 2 was taken during an overcast day in August, 1985.

The following is a detailed description of my new impatiens cultivar based on plants produced under commercial practices in Ashtabula, Ohio, grown in 5.5" green plastic pots during the winter/spring of 1983, and then replanted into a 15" red wood tub and grown outside during the summer of 1983. Color references are made to The Royal Horticultural Society Colour Chart except where general terms of ordinary dictionary significance are used.

Parentage: Mikkelsen Seedling No. 80-439-4×Mikkelsen Seedling No. 80-428-2.

Propagation:

(A) *Type cutting.*—Stem 15 mm long will develop 5 to 6 mm long in 18 to 21 days.

(B) *Time to root.*—8 to 10 days at 23° C. summer, 10 to 12 days at 20° C. winter.

(C) *Rooting habit.*—Large mass of fiberous roots from the stem.

Plant description:

(A) *Form.*—Symmetrical, bush shaped, and very dense flowering herb. The stems are reddish purple in color.

(B) *Habit of growth.*—Vigorous, highly self-branching, semi-compact bush, with continuous flowering.

(C) *Foliage description.*—Broad semi-short leaves, bronze purple in color with a distinct golden bronze at the midrib with red veins; small hairs on upper surface of leaves. (1) Size: 7.5 to 7.75 cm in length×3.0 to 3.25 cm in width. (2) Shape: Lanceolate to ovate, acuminate apex with acute base. (3) Texture: Rugose and pubescent upper side, glabrous under side. (4) Margin: Serrated, finely ciliated. (5) Color: Young foliage, top side 137A, under side 59A. Mature foliage, top side lighter than 139A, under side 185A. (6) Venation: Pinnate and red in color.

Flowering description:

(A) *Flowering habits.*—Flowers continuously from leaf whorl in progressive and orderly manner, taking 5 to 7 days from bud showing color to bloom; flowers last 2 to 3 weeks.

(B) *Natural flowering season.*—Indeterminant and continuous; quantity of flowers increase with increasing levels of light intensity and duration.

(C) *Flower buds.*—Ellipsoidal, flowers perfect, pink spur 4.0 to 4.25 cm long on mature bud with throat behind ovary and originating from the major sepal.

(D) *Flowers borne.*—On individual short pedicels from whorl of five leaves progressively around the whorl as leaves and buds develop, and remaining just inside the leaf canopy.

(E) *Quantity of flowers.*—Floriferous; flowering is continuous so that tight buds to mature blooms are visible at the same time in large numbers.

(F) *Petals.*—(1) Shape: Heart shaped, all five petals approximately equal in size, very symmetrical with overlapping. (2) Color: Top side in summer when opening, 49C infused with 40C, intensifying during maturity to 49B infused with 40C; under side, 49A (uniform and not bicolor), fading to 49B. (3) Number of petals: Five (5) in number. (4) Size of flowers: 5 cm to 5.25 cm.

(G) Reproductive organs.—(1) Stamens: Five (5) in number. (a) Anther shape: Hooded, color 57C. (b) Pollen color: Cream. (2) Pistils: (a) Stigma shape: Five, segmented column-shaped, white in color. (b) Style color: Clear. (c) Ovaries, Five (5) in number, celled, size 4 mm until fertilized, green with some purple in color.

Disease resistance: No significant disease or insect problems have been seen to date.

Summary of important characteristics of new cultivar: (1) Distinct bicolor of flower. (2) Distinct color of variegation. (3) Relatively short, broad leaves. (4) High degree of self-branching. (5) Upper surface of leaves are pubescent.

I claim:

1. A new and distinct cultivar of New Guinea Impatiens plant named Twilight, as described and illustrated, and particularly characterized by its distinct red and light pink bicolor flowers, distinct variegated leaves, vigorous, highly self-branching dense bush growth habit making it useful for pot, hanging basket and bedding plant use; and by its adaptability to various environments of use.

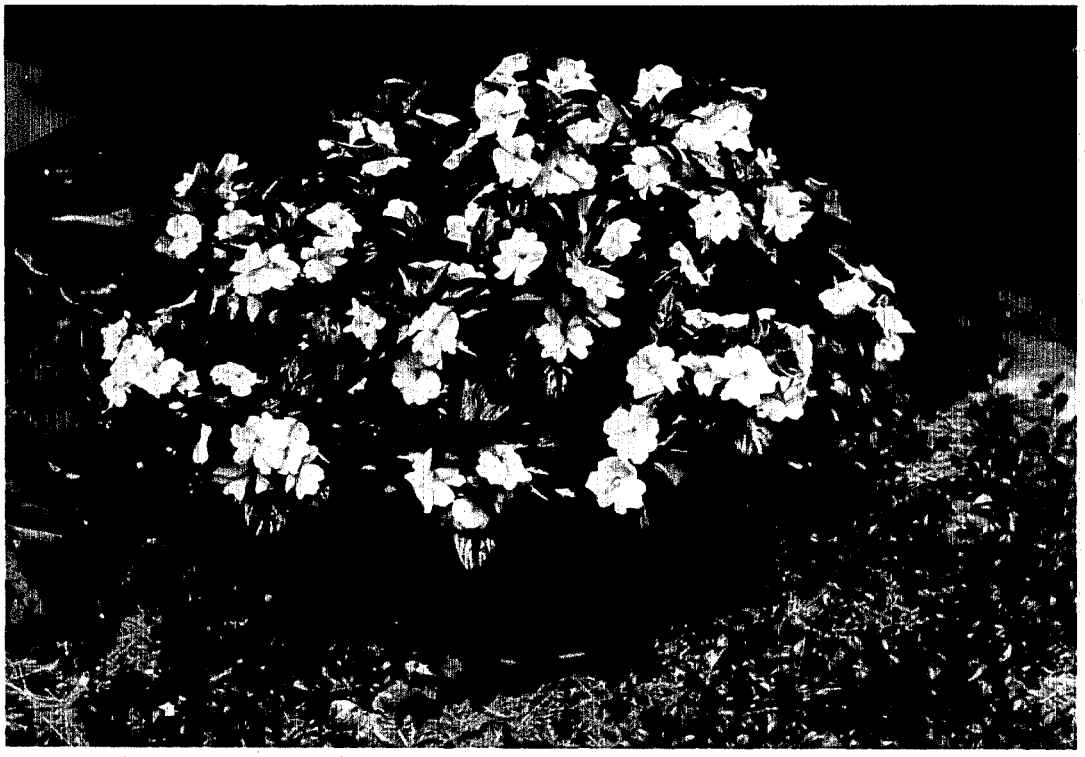

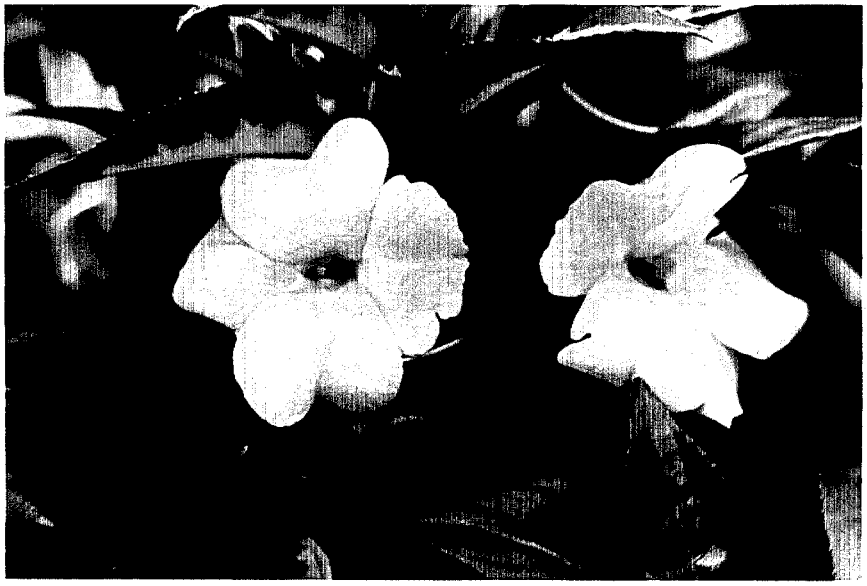

* * * * *